United States Patent
Hintze-Bruening et al.

(10) Patent No.: US 9,932,442 B2
(45) Date of Patent: Apr. 3, 2018

(54) CARBOXY-FUNCTIONAL POLYESTER AND DIESTER DERIVATIVES

(71) Applicant: BASF Coatings GmbH, Muenster (DE)

(72) Inventors: Horst Hintze-Bruening, Muenster (DE); Elke Austrup, Nordkirchen (DE); Thomas Lohmeier, Rahden (DE); Charles Frederick James Faul, Bristol (GB); Alex Matthew Oliver, Lemington Spa (GB)

(73) Assignee: BASF Coatings GmbH, Muenster (DE)

( * ) Notice: Subject to any disclaimer, the term of this patent is extended or adjusted under 35 U.S.C. 154(b) by 68 days.

(21) Appl. No.: 14/912,268

(22) PCT Filed: Jul. 16, 2014

(86) PCT No.: PCT/EP2014/065260
§ 371 (c)(1),
(2) Date: Feb. 16, 2016

(87) PCT Pub. No.: WO2015/022134
PCT Pub. Date: Feb. 19, 2015

(65) Prior Publication Data
US 2016/0208043 A1    Jul. 21, 2016

(30) Foreign Application Priority Data

Aug. 16, 2013   (EP) ................... 13180646

(51) Int. Cl.
| | |
|---|---|
| C08G 63/91 | (2006.01) |
| C08G 63/02 | (2006.01) |
| C08L 67/02 | (2006.01) |
| C07C 67/08 | (2006.01) |
| C08L 67/00 | (2006.01) |

(52) U.S. Cl.
CPC .............. C08G 63/91 (2013.01); C07C 67/08 (2013.01); C08G 63/916 (2013.01); C08L 67/00 (2013.01)

(58) Field of Classification Search
USPC ....................................................... 524/601
See application file for complete search history.

(56) References Cited

U.S. PATENT DOCUMENTS

| | | | |
|---|---|---|---|
| 4,089,879 A | 5/1978 | Naskar et al. | |
| 4,504,609 A * | 3/1985 | Kuwajima ............ | C09D 5/02 523/501 |
| 4,791,168 A * | 12/1988 | Salatin ............... | C08G 18/0823 427/407.1 |
| 5,244,699 A * | 9/1993 | Jones .................. | C08G 81/00 525/123 |
| 6,242,559 B1 | 6/2001 | Ranka | |
| 6,388,024 B1 * | 5/2002 | Van Gaalen ......... | C08G 59/12 525/437 |
| 2004/0229048 A1 * | 11/2004 | Kesselmayer ........ | C08G 18/12 428/423.1 |
| 2005/0176881 A1 | 8/2005 | Bheda et al. | |
| 2007/0160799 A1 | 7/2007 | Nguyen | |
| 2012/0264858 A1 | 10/2012 | Hintze-Bruening et al. | |

FOREIGN PATENT DOCUMENTS

| | | |
|---|---|---|
| GB | 1 526 290 A | 9/1978 |
| JP | 10-67708 | * 3/1998 |
| WO | 99/11693 A1 | 3/1999 |
| WO | 2010/130308 A1 | 11/2010 |
| WO | 2010/130312 A1 | 11/2010 |
| WO | 2013/056846 A1 | 4/2013 |

OTHER PUBLICATIONS

English abstract of JP 10067708, Mar. 10, 1998, Japan, 4 pages.*
International Search Report dated Oct. 9, 2014 for PCT/EP2014/065260 filed on Jul. 16, 2014.

* cited by examiner

*Primary Examiner* — Tae H Yoon
(74) *Attorney, Agent, or Firm* — Oblon, McClelland, Maier & Neustadt, L.L.P.

(57) ABSTRACT

The present invention relates to new carboxy-functional polyester and diester derivatives preparable by ring-opening reaction of (A) at least one anhydride of the formula (I)

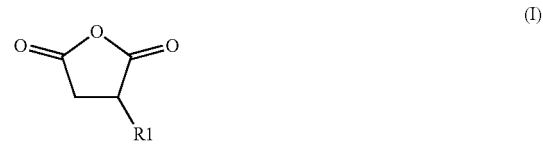

(I)

where $R_1$=H, $C_1$ to $C_{24}$ alkyl, or $C_2$ to $C_{24}$ alkenyl with (B) at least one hydroxy-functional component, where (B1) the polyester derivatives are prepared using at least one linear hydroxy-functional polyester prepared using 7 to 95 mol %, based on the total amount of the monomers used in preparing the polyester (B1), of at least one difunctional monomer (b1) with aliphatic groups with 12 to 70 carbon atoms between the functional groups, and (B2) the diester derivatives are prepared using at least one dihydroxy-functional component which has an aliphatic group with 12 to 70 carbon atoms between the hydroxyl groups. The present invention further relates to aqueous compositions comprising at least one such polyester derivative and/or diester derivative, and water. The present invention relates, moreover, to the use of the polyester and/or diester derivatives for producing liquid-crystalline phases.

16 Claims, 5 Drawing Sheets

CARBOXY-FUNCTIONAL POLYESTER AND DIESTER DERIVATIVES

This application is a national stage filing under 35 U.S.C. 371 of PCT/EP2014/065260, filed Jul. 16, 2014, which claims priority to EP 13180646.5, filed Aug. 16, 2013, the disclosures of which are incorporated by references in their entirety herein.

The present invention relates to new carboxy-functional polyester derivatives and diester derivatives which are preparable by ring-opening reaction of an anhydride with a hydroxy-functional precursor. While the hydroxy-functional precursor has a hydrophobic character, the ring-opening reaction produces free carboxyl groups and, accordingly, an amphiphilic molecular character in the resulting polyester or diester derivative. The polyester and diester derivatives of the invention have outstanding performance properties. In particular it is possible, with the polyester and diester derivatives of the invention, to prepare aqueous compositions which have liquid-crystalline properties. This means, in other words, that compositions which comprise the polyester and diester derivatives of the invention, and also water, form liquid-crystalline phases.

PRIOR ART

A wide variety of different polyesters, and also diester derivatives, and their use, are known. Polyesters in particular are used for example as film formers in coating materials such as paints and inks. Such esters are likewise used for example, depending on composition and properties, as additives for producing any of a very wide variety of different properties in coating materials such as paints and inks. In this context it is possible for such polyester and diester derivatives to develop their properties through specific combination with further components such as additives, pigments and/or fillers.

Thus WO 2010/130312 A1 discloses the use of a specific combination of a special polyester with laminar inorganic particles, examples being mixed oxides, in aqueous systems, these systems having liquid-crystalline properties. These liquid-crystalline systems, when used in aqueous coating materials, lead to outstanding stone-chip resistance on the part of the coatings produced using these coating materials. WO 2010/130308 likewise discloses a combination of a polyester and mixed hydroxides and/or hydrotalcites in aqueous phase, and the use of these liquid-crystalline systems in aqueous waterborne effect paints. The optical properties, especially the attainment of metallic effects (flop) and brightness, of paint systems produced using the effect paints are outstanding.

Liquid-crystalline systems combine typical properties of a liquid, more particularly a certain flowability or fluidity, with typical properties of a crystal, more particularly, therefore, a certain structural anisotropy. Such systems may, for example, be thermotropic, meaning that their liquid-crystalline properties occur temperature-dependently. Also found are lyotropic systems. In such systems, in the presence of a solvent, water for example, and amphiphilic organic components such as surfactants, a liquid-crystallinity is achieved within certain concentration ranges. When structural anisotropy is present there is generally also an optical anisotropy, meaning that such systems display the known phenomenon of birefringence. For different polarization and direction of the irradiated light, therefore, the systems exhibit different refractive indices. As a result of the birefringence, complete extinction does not occur under the polarization microscope (i.e., crossed polarizers, namely the primary filter, or linear polarizer of the light from the light source, and the secondary filter, or analyzer, which is rotated by 90° relative to the primary filter), despite the stated filter arrangement, and in contrast to what is the case with purely isotropic systems; instead, a part of the light passes through the analyzer and can therefore be detected.

The effects of liquid-crystallinity and of the attendant balance between anisotropy and fluidity on different properties, such as pigment orientation and/or rheology, for example, makes the corresponding systems particularly productive. On the one hand it is possible to utilize the advantages which exist as a result of the liquid character, especially the good formulation capacity and processing properties. On the other hand, as a result of the crystallinity and the corresponding anisotropy, the corresponding properties of solid components can be utilized simultaneously. Consequently a need exists for the provision of new components and compounds with which it is possible to attain the stated liquid-crystallinity. In aqueous systems in particular, which are very relevant particularly in the paint industry sector, on account of their valuable environmental profile, there is great interest in the provision of such components.

PROBLEM

The problem addressed by the present invention was therefore that of providing new components with which systems having particularly pronounced liquid-crystalline properties can be produced. The intention more particularly was to provide components which are able to lead to these liquid-crystalline properties in aqueous systems. These systems ought to be extremely simple to prepare, and the achievement of liquid-crystallinity ought to be made possible even without costly and inconvenient addition of further compounds. In other words, the components ought on their own, and without the addition of further compounds, to lead to liquid-crystalline phases in or with water. Although combination with other compounds may be appropriate in various cases, therefore, the possibility ought to be provided of using the components on their own in water and at the same time forming liquid-crystalline phases. In this way, the intention is that success should be achieved in uniting the anisotropic, ordered properties of crystalline systems with the good formulation capacity inherent in a liquid or in a fluid system.

SOLUTION

It has been found that the stated problems could be solved by means of new carboxy-functional polyester and diester derivatives which are preparable by ring-opening reaction of
(A) at least one anhydride of the formula (I)

(I)

where $R_1$=H, $C_1$ to $C_{48}$ alkyl, or $C_2$ to $C_{48}$ alkenyl
with
(B) at least one hydroxy-functional component, where
(B1) the polyester derivatives are prepared using at least one linear hydroxy-functional polyester prepared using 7 to 95 mol %, based on the total amount of the monomers used in preparing the polyester (B1), of at least one difunctional monomer (b1) with aliphatic groups with 12 to 70 carbon atoms between the functional groups, and (B2) the diester derivatives are prepared using at least one dihydroxy-functional component which has an aliphatic group with 12 to 70 carbon atoms between the hydroxyl groups.

The new carboxy-functional polyester and diester derivatives are also referred to below as polyester and diester derivatives of the invention. Preferred embodiments of the polyester and diester derivatives of the invention can be found in the description following on further below, and also in the dependent claims.

The present invention additionally provides a process for preparing the polyester and diester derivatives of the invention, by reacting (A) at least one anhydride of the formula (I)

(I)

where $R_1$=H, $C_1$ to $C_{48}$ alkyl, or $C_2$ to $C_{48}$ alkenyl with (B) at least one hydroxy-functional component, with opening of the anhydride ring, where (B1) the polyester derivatives are prepared using at least one linear hydroxy-functional polyester prepared using 7 to 95 mol %, based on the total amount of the monomers used in preparing the polyester (B1), of at least one difunctional monomer (b1) with aliphatic groups with 12 to 70 carbon atoms between the functional groups, and (B2) the diester derivatives are prepared using at least one dihydroxy-functional component which has an aliphatic group with 12 to 70 carbon atoms between the hydroxyl groups.

Additionally provided with the present invention is an aqueous composition comprising at least one polyester and/or diester derivative of the invention, and water.

Likewise provided with the present invention is a process for preparing liquid-crystalline phases, using at least one polyester and/or diester derivative of the invention, and also the use of the polyester and diester derivatives of the invention for producing liquid-crystalline phases, more particularly their use for producing such phases with water.

It has been found more particularly that a particularly pronounced liquid-crystallinity in aqueous systems can be achieved with the polyester and diester derivatives of the invention. These aqueous systems can be prepared in a very simple way. The liquid-crystallinity can also be achieved without the addition of further compounds, and so the addition of further compounds is necessary only when such addition is desired in a particular case, in order, for example, to attain various further performance properties. The systems therefore combine the anisotropic, ordered properties of crystalline systems with the good formulation capacity inherent in a liquid or in a fluid system.

DETAILED DESCRIPTION

Anhydride (A)

The polyester and diester derivatives of the invention are prepared using at least one anhydride (A) of the formula (I) below:

(I)

where $R_1$=H, $C_1$ to $C_{48}$ alkyl, or $C_2$ to $C_{48}$ alkenyl, preferably $C_6$ to $C_{48}$ alkyl, or $C_6$ to $C_{48}$ alkenyl, more preferably $C_6$ to $C_{48}$ alkenyl, and very preferably $C_6$ to $C_{24}$ alkenyl.

The anhydride (A) therefore comprises succinic anhydride or succinic anhydride derivatives that are substituted accordingly by alkyl and/or alkenyl, and preferably alkenyl-substituted succinic acid derivatives. The alkyl and alkylene radicals may be linear or branched. The position of the carbon-carbon double bond in the alkylene radicals is arbitrary per se.

The succinic anhydride derivatives are prepared preferably by reaction of maleic anhydride with alpha-olefins. The initial product of this reaction is a corresponding alkenyl-modified succinic anhydride derivative, which then can also be used in the sense of the present invention. In beta-gamma position as viewed from the anhydride ring, a derivative of this kind then contains a carbon-carbon double bond. An example is 2-octenylsuccinic anhydride, which, moreover, is used with very particular preference for the purposes of the present invention. The underlying reaction mechanism (ene reaction) is known to the skilled person; corresponding reaction conditions can be readily selected and adapted. Corresponding compounds can also be acquired commercially.

It is also possible, for example, for a succinic acid derivative of this kind, such as 2-octenylsuccinic anhydride, to be reacted further with other alpha-olefins present in the reaction solution, such as 1-octene, via an ene reaction, and in that way for branching to be incorporated into the alkenyl chain by attachment of the further molecule of the alpha-olefin. The resulting mixtures of succinic anhydride derivatives can likewise be acquired commercially and can likewise be used for preparing the polyester and diester derivatives of the invention. Preferably, however, molecularly uniform derivatives are used. Such uniform derivatives may, as already indicated above, also be acquired commercially.

Component (B)

Component (B) used for the ring-opening reaction is hydroxy-functional. This leads to success in the ring-opening reaction with the anhydride, as described in detail later on below, with formation of ester bonds and free carboxyl groups.

The polyester derivatives are prepared using, as component (B), linear, hydroxy-functional polyesters (B1).

Generally speaking, a polyester is a polymeric organic compound which is prepared using polyhydric organic alcohols and polybasic organic carboxylic acids. These alcohols and carboxylic acids are linked to one another by esterification, in other words by condensation reactions. The polyesters, accordingly, are classed in general with the group of the polycondensation resins. For the preparation of polyesters it is also known to be possible, instead of or in addition to the corresponding organic carboxylic acids, to use the anhydrides of the carboxylic acids, especially the anhydrides of dicarboxylic acids. In the context of the present invention, therefore, the designation "anhydride" refers to a carboxylic anhydride. Likewise possible is the preparation through the use of hydroxycarboxylic acids or of lactones that are derived from the hydroxycarboxylic acids by intramolecular esterification.

Linear products such as the polyesters (B1) for use in accordance with the invention are obtained in particular when using difunctional starting components (diols, dicarboxylic acids). For the purposes of the present invention, therefore, the expression "linear polyester" means that the polymer backbone, in other words, the sequence of ester bonds which make up the linkage between the individual polyester building blocks, has a linear character. The individual compounds (monomers) used for the preparation therefore possess in each case two functional groups capable of ester bonding—in other words, more particularly, hydroxyl groups, carboxyl groups, and/or anhydride groups. The linkage then produces a polyester chain or a linear polyester. Preference is given accordingly to using only minor amounts (less than 5 mol %, preferably less than 2 mol %, based on the total amount of the monomers used in preparing the polyester (B1)) of monomers which have more than two functional groups capable of ester bonding, since branches can be inserted into the polymer molecules by this means. With very particular preference no monomers having more than two functional groups capable of ester bonding are used.

Monomers used in preparing the polyesters (B1) are, for the purposes of the present invention, all individual starting compounds which are used in the preparation of these polyesters (B1) and whose basic structures are incorporated into the polyester. These are, for example, typical monomeric compounds having two corresponding functional groups, such as 1,6-hexanediol, for example. As starting compounds for preparing polyesters it is also known, however, to be possible to use compounds which have themselves already been prepared by linkage of two or more individual molecules, such linkage being possible in any of a very wide variety of different ways. Reference may be made, for example, to the dimeric fatty acids described below. Even these compounds, however, are identified as starting compounds, which are incorporated into the polyester by means of corresponding polymerization reactions and which then make up a non-independent component of the polyester. These starting compounds as well, accordingly, are termed monomers.

The polyesters (B1) used for preparing the polyester derivatives of the invention are polyesters prepared using 7 to 95 mol %, based on the monomers used in preparing the polyester (B1), of at least one difunctional monomer (b1) with aliphatic groups with 12 to 70 carbon atoms between the functional groups.

Aliphatic compounds are known to be acyclic or cyclic, saturated or unsaturated hydrocarbon compounds which are not aromatic. The term "aliphatic compound" therefore encompasses acyclic and cyclic aliphatics, and is taken to be a corresponding generic term in the context of the present invention as well. The acyclic aliphatics may be linear or branched. Linear in this context means, as is known, that the compound in question has no branches with regard to the carbon chain, the carbon atoms instead being arranged exclusively in a linear sequence in a chain. Branched or nonlinear therefore means, in the context of the present invention, that the compound under consideration in each case has branching in the carbon chain—in other words, in contrast to what is the case for the linear compounds, at least one carbon atom in the compound in question is a tertiary or quaternary carbon atom. Cyclic aliphatics or cycloaliphatics are those compounds in which at least some of the carbon atoms present are linked in the molecule in such a way that one or more rings are formed. Besides the one or more rings, of course, there may be further acyclic linear or branched aliphatic groups present in a cycloaliphatic compound.

An aliphatic group, therefore, is a group which fulfills the requirements set out above for the aliphatic compounds, but is only part of a molecule. Besides the aliphatic group, the molecule in question also contains other groups such as, for example, functional groups. Functional groups for the purposes of the present invention are terminal groups which contain heteroatoms such as oxygen, sulfur and/or nitrogen, examples being hydroxyl groups or carboxyl groups. Also present, of course, may be bridging heteroatoms or bridging groups containing heteroatoms. Ether bonds may be cited as an example.

Monomers with aliphatic groups between functional groups is a term used accordingly for those monomers which in addition to the corresponding functional groups have aliphatic groups disposed between the functional groups. The monomers therefore consist of corresponding functional groups and aliphatic groups, thus containing only the (terminal) functional groups and the aliphatic groups.

The functional groups of the difunctional monomers (b1) are evidently groups capable of forming ester bonds, in other words, more particularly, hydroxyl groups and/or carboxylic acid groups and also anhydride groups. The monomers (b1) are therefore preferably diols, dicarboxylic acids and/or hydroxycarboxylic acids, and also anhydrides, more preferably diols and/or dicarboxylic acids.

The aliphatic groups of the monomers (b1) possess 12 to 70, preferably 13 to 50, and more preferably 14 to 40 carbon atoms.

The polyesters (B1) are prepared using, based on the total amount of the monomers used in preparing the polyester (B1), 7 to 95 mol %, preferably 9 to 90 mol %, more preferably 10 to 85 mol % of the monomers (b1).

In one especially preferred embodiment of the present invention, the polyesters (B1) are prepared using, based on the total amount of the monomers used in preparing the polyester (B1), 50 to 95 mol %, preferably 60 to 90 mol %, more preferably 70 to 85 mol % of the monomers (b1).

Preferred monomers (b1) are, for example, fully hydrogenated bisphenols, an example being the fully hydrogenated bisphenol A. Equally preferred are dimeric aliphatic fatty alcohols and/or dimeric aliphatic fatty acids, among which the dimeric aliphatic fatty acids are preferred. In a further preferred embodiment both dimeric aliphatic fatty acids and dimeric aliphatic fatty alcohols are used together as monomers (b1).

In a further, particularly preferred embodiment, the present invention uses dimeric aliphatic fatty acids having 24 to 40 carbon atoms and also fully hydrogenated bisphenol A as monomers (b1).

Dimeric aliphatic fatty acids are preparable by catalytic dimerization of unsaturated, plant-derived fatty acids, the unsaturated fatty acids containing 18 carbon atoms being employed more particularly in the preparation, the product thus having 36 carbon atoms. Linking proceeds primarily in accordance with the Diels-Alder type and the ene reaction, and results in mixtures of, for example, cycloaliphatic and linear-aliphatic dimeric fatty acids, which may be saturated or unsaturated depending on mechanism and/or on optional subsequent hydrogenation. As well as the aliphatic adducts (b1), these mixtures usually also include certain fractions of aromatic and/or mixed aliphatic-aromatic groups.

Accordingly, if dimeric aliphatic fatty acids are among the monomers (b1) used, the polyesters (B1) are preferably prepared using not only these monomers (b1) but also, preferably, difunctional monomers (b2) which likewise contain 12 to 70 carbon atoms, preferably 13 to 50, and more preferably 14 to 40 carbon atoms between the functional groups, but which are not purely aliphatic, but instead at least proportionally are aromatic as well. These groups are therefore preferably mixed aliphatic-aromatic groups—that is, the groups with 12 to 70 carbon atoms contain aliphatic and aromatic parts.

The stated dimeric fatty acids or monomers (b1) may be obtained in corresponding mixtures with monomers (b2) as commercial products. Examples include the dimeric aliphatic fatty acids of the Pripol® series from Unichema.

The molar ratio of the dimeric aliphatic fatty acids (b1) to the monomers (b2) in these commercial products is preferably from 2 to 6, more particularly preferably 3 to 5. The reason is that such proportions regularly result in the above-described catalytic dimerization of fatty acids.

In one preferred embodiment, accordingly, mixtures of dimeric aliphatic fatty acids for use as monomers (b1) with monomers (b2) are used. The molar ratio of these mixtures is preferably from 2 to 6, more preferably from 3 to 5.

Depending on the desired amount of dimeric aliphatic fatty acids to be used as monomers (b1), based on the total amount of the monomers used in preparing the polyester (B1), therefore, the monomers (b2) are used in fractions of, for example, 1 to 10 mol %, preferably 2 to 5 mol %, in preparing the polyester (B1). According to what has been said above, the fraction of the monomers (b2) is dependent on whether and, if so, in which fraction dimeric fatty acids, and hence the stated commercial products, are used as monomers (b1). If, for example, hydrogenated bisphenols and/or dimeric aliphatic fatty alcohols (which are generally obtained by hydrogenation of dimeric aliphatic fatty acids, in which case the monomers (b2) that are generally also present are likewise hydrogenated and hence reduced to monomers (b1), namely dimeric aliphatic fatty alcohols) are used exclusively or predominantly as monomers (b1), then the fraction of monomers (b2) is correspondingly lower. Where dimeric aliphatic fatty acids are used exclusively or predominantly, the fractions of the monomers (b2) are therefore, evidently, in general higher.

Further building blocks which can be used in preparing the polyester (B1) are preferably the following monomers:
 (b3) linear aliphatic and/or cycloaliphatic diols having 2 to 11 carbon atoms, such as, in particular, ethylene glycol, diethylene glycol, 1,3-propanediol, dipropylene glycol, 1,4-butanediol, 1,6-hexanediol, 1,4-cyclohexanediol and/or 1,4-dimethylolcyclohexane, preferably 1,4-butanediol and/or 1,6-hexanediol, these diols, in preparing the polyester (B1), being used preferably in fractions of, for example, 0 to 40 mol %, preferably 0 to 35 mol %, based on the total amount of the monomers used in preparing the polyester (B1),
 (b4) branched aliphatic diols having 4 to 11 carbon atoms, such as, in particular, neopentyl glycol, 2-methyl-2-propylpropanediol, 2-ethyl-2-butylpropane-diol, 2,2,4-trimethyl-1,5-pentanediol, 2,2,5-trimethyl-1,6-hexanediol, preferably neopentyl glycol, these diols being used, in preparing the polyester (B1), preferably in fractions of, for example, 0 to 45 mol %, preferably 0 to 40 mol %, based on the total amount of the monomers used in preparing the polyester (B1),
 (b5) linear aliphatic, cycloaliphatic and/or aromatic dicarboxylic acids having 4 to 12 carbon atoms, such as, in particular, oxalic acid, malonic acid, succinic acid, glutaric acid, adipic acid, sebacic acid, maleic acid, fumaric acid, isophthalic acid, terephthalic acid, orthophthalic acid, tetrahydrophthalic acid, hexahydrophthalic acid, 1,4-cyclohexanedioic acid, and/or their anhydrides, preferably hexahydrophthalic acid, these dicarboxylic acids being used, in preparing the polyester (B1), preferably in fractions of, for example, 5 to 30 mol %, preferably 10 to 25 mol %, based on the total amount of the monomers used in preparing the polyester (B1),
 optionally further monomers (b6) having for example 12 to 70 carbon atoms and comprising bridging heteroatoms and/or bridging groups containing heteroatoms, in fractions of, for example, 0 to 10 mol %, based on the total amount of the monomers used in preparing the polyester (B1).

The monomers used for preparing the polyesters (B1) are used preferably in fractions such that the molar ratio of hydroxyl groups to carboxylic acid groups is greater than 1.5, more particularly between 1.5 and 3, very preferably between 1.7 and 2.7, and, in one specially preferred embodiment, between 1.8 and 2.5. The calculation of this molar ratio includes the two potential carboxylic acid groups of an anhydride monomer on the sides of the carboxylic acid groups. Through the choice of these preferred ratios particularly good success is achieved in generating the hydroxy-functionality of the polyesters (B1)—more particularly, in generating two terminal hydroxyl groups for the subsequent ring-opening reaction with the anhydride (A). Systems or polyester derivatives which are prepared using such polyesters (B1) and in which the polyester (B1) is anhydride-functionalized on both sides have particularly good properties as regards liquid-crystallinity, and are therefore particularly preferred. The stated molar ratios are understood as ratios calculated from the respective functionality and the molecular weight of the starting compounds (monomers) employed.

The polyester (B1) is hydroxy-functional. Preferably it has exactly two terminal hydroxyl groups per molecule, thus meaning that the linear polyester chain is closed off on both sides by a hydroxyl group.

The polyester (B1) preferably has an OH number of 80 to 200, more preferably of 100 to 190, very preferably of 120 to 180 mg KOH/g. The OH number for the purposes of the present invention is determined in accordance with DIN 53240. The acid number of the polyester (B1) is preferably low and more preferably is in the range from 0 to 50, preferably 2 to 30, very preferably from 5 to 20 mg KOH/g. Preferably, therefore, the polyester (B1) contains only a very small fraction of carboxyl groups—for example, merely as a result of synthesis, residual carboxyl groups which remain as a result of an incomplete conversion. The acid number for the purposes of the present invention is measured in accordance with DIN EN ISO 3682. For the purposes of the present invention, the reporting of an OH number or acid number for a polymer should always be understood in relation to the corresponding nonvolatile fraction. The nonvolatile fraction (solids) of a component, as for example of a dispersion of a polymer such as a polyester, is determined for the purposes of the present invention in accordance with DIN EN ISO 3251, with an initial mass of 1.0 g of the respective component, over a test duration of 60 minutes and a temperature of 125° C.

The number-average molecular weight of the polyester (B1) is preferably in the range from 400 to 2000, more preferably from 600 to 1500 g/mol, very preferably 700 to 1200 g/mol, while the weight-average molecular weight is preferably in the range from 1200 to 3000 g/mol, more preferably 1500 to 2500 g/mol. For the purposes of the present invention, the molecular weights are determined by means of GPC analysis using THF (+0.1% acetic acid) as eluent (1 ml/min) on a styrene-divinylbenzene column combination. The calibration is performed using polystyrene standards.

The preparation of the polyesters (B1) and hence the reaction of the monomers takes place in accordance with the widely known methods of polyester chemistry, the skilled person likewise being aware of how the conditions must be selected in order, for example, to obtain the abovementioned preferred properties, such as OH number and acid number. The reaction may take place, for example, in bulk or in solution with typical organic solvents, at temperatures of, for example, 50° C. to 300° C., preferably 100° C. to 290° C., more particularly 140° C. to 280° C. Through reaction temperatures of more than 140° C. in particular it is possible to ensure that with simultaneous use of anhydrides and free carboxylic acids there is also an effective reaction of free carboxylic acids, in other words an effective incorporation of the corresponding monomers into the polyester scaffold. It will be appreciated that typical catalysts can also be employed, such as sulfuric acid, sulfonic acids and/or tetraalkyltitanates, zinc alkoxylates and/or tin alkoxylates, dialkyltin oxides, or organic salts of the dialkyltin oxides.

Employed as component (B) for preparing the diester derivatives are dihydroxy-functional components (B2), a component (B2) having an aliphatic group with 12 to 70 carbon atoms between the hydroxyl groups. As far as the aliphatic group and the corresponding definitions are concerned, component (B2) is subjected to the same description as already given above with regard to the monomer (b1). Component (B2) thus consists of an aliphatic group having 12 to 70 carbon atoms and the hydroxyl groups. The component (B2) preferably has 13 to 50 and more preferably 14 to 40 carbon atoms. As component (B2), preference is given to using dihydroxy-functional components in which the hydroxyl groups are secondary. It has emerged that by this means, in particular, the hydrolysis stability of the diester derivatives of the invention in aqueous medium can be improved, in other words, therefore, in particular, the hydrolysis stability of the ester bond which comes about as a result of the ring-opening reaction, described later on below, of the hydroxyl groups of component (B2) with the anhydride (A).

Preferred components (B2) are therefore, for example, the fully hydrogenated bisphenols. Especially preferred is the fully hydrogenated bisphenol A.

In certain embodiments of the present invention, however, the use of dimeric aliphatic fatty alcohols, or a combination of fully hydrogenated bisphenols, more particularly fully hydrogenated bisphenol A, and dimeric aliphatic fatty alcohols, may be of advantage.

The Ring-Opening Reaction for Preparing the Polyester and Diester Derivatives of the Invention The polyester and diester derivatives of the invention are prepared by ring-opening reaction of an anhydride (A), of the formula (I) shown and elucidated earlier on above, with a hydroxy-functional component (B), as described above.

As the skilled person is aware, a reaction of this kind between an anhydride and a hydroxyl group takes place with formation of an ester bond and of a carboxyl group. The hydroxy-functional component (B)—that is, then, a specific linear hydroxy-functional polyester (B1), preferably a dihydroxy-functional polyester (B1)—or a specific dihydroxy-functional component (B2) is therefore modified, with formation of an ester bond, with a corresponding carboxy-functional terminal group, to form a polyester or diester derivative of the invention.

In the context of the present invention, therefore, the expression "ring-opening reaction" is understood to mean that apart from specifically this ring-opening reaction, no further reactions occur, i.e., more particularly, no further reactions of the carboxylic acid groups, formed by the ring-opening reaction, with further molecules, still present in the reaction mixture, of the hydroxy-functional component (B). As the skilled person is aware, a condensation reaction of this kind, with formation of a further ester bond, would in principle be possible. Any such further reaction, however, may be readily prevented, in a way likewise known to the skilled person, through appropriately adapted reaction regime. As is known, an anhydride, owing to the ring tension and to the consequent higher energy release on reaction with a hydroxyl group, has a higher reactivity than a free carboxylic acid group. Thus, for example, it is possible to operate at reaction temperatures which permit the ring-opening reaction but do not permit any further condensation reactions. Moreover, through the deliberate use or deliberate omission, more particularly the omission, of catalysts, examples being typical acid catalysts or dibutyltin laurate, the desired reaction regime can be ensured. Moreover, the addition or omission of water or the use of water separators, for example, is known to have influence on the different reactivities, since while water is released in the typical condensation reaction between carboxylic acid and alcohol, this is not the case for the reaction of anhydride and alcohol. The skilled person knows how to adapt these conditions accordingly.

The ring-opening reaction of the invention therefore produces a polyester or diester derivative which comprises carboxylic acid groups, or additional carboxylic acid groups. The polyester or diester derivative of the invention preferably has such carboxy-functional groups at both ends. This means, therefore, that in the course of the reaction, preferably, component (B), and/or the molar ratio of the anhydride used to the hydroxyl groups of component (B), is selected such that the polyester or diester derivative of the invention carries corresponding carboxy-functional groups at both ends. A polyester or diester derivative of the invention preferably possesses precisely two carboxylic acid groups per molecule.

It is preferable, accordingly, in the polyester and diester derivatives of the invention, for the molecular unit originating from component (B) to be located in the core or in the center of the polyester or diester derivative of the invention, while the molecular units originating from the anhydride are present in the form of side groups and/or end groups. With particular preference the polyester and diester derivatives of the invention have precisely two end groups originating from the anhydride. This therefore means in particular that component (B1) preferably has two terminal hydroxyl groups. These groups may then both react with the anhydride (A). In terms of component (B2) as well, therefore, there is preferably complete reaction of the two hydroxyl groups present. As described earlier on above, component (B) comprises specific aliphatic groups having at least 12 carbon atoms. The consequent hydrophobic character of component (B) then contributes to a particular amphiphilic character, with the anhydride molecules attached terminally on both sides or with the two corresponding free carboxyl groups, which account for a hydrophilic character. Whereas the more hydrophobic unit is located in the center of the molecule, both terminal, opposite side groups are hydrophilic. These specific polyester and diester derivatives possess particularly advantageous properties in terms of their liquid-crystalline behavior.

In the reaction it is preferable to use precisely one kind of anhydride (A) and precisely one kind of hydroxy-functional component (B).

As the skilled person is aware, the abovementioned reactions and reaction regimes, for purely statistical reasons, also produce products which do not have the idealized structure described. Generally, for example, byproducts are likely which form through a further reaction of the resultant polyester and diester derivatives with molecules of component (B) that are still present, or products which are functionalized on only one side in spite of the preferred two-sided functionalization. Equally possible is a minor reaction of the anhydride (A) with water or atmospheric moisture, if, for example, operation is not entirely water-free or not with exclusion of atmospheric conditions (atmospheric moisture) during the reaction. There will also be unreacted starting components in the reaction mixture. In spite of this, the reaction regime described makes it possible readily to obtain the likewise-described polyester and diester derivatives as principal products. These derivatives can also be used without further purification.

The ring-opening reaction of the anhydride (A) with the component (B) may take place by different methods known to the skilled person, with observance of the above-described prevention of the further reaction of the resulting polyester or diester derivatives with molecules of the hydroxy-functional component (B). The reaction may take place, for example, in bulk or in solution, preferably in solution with organic solvents such as 4-methyl-2-pentanone or other common solvents, at temperatures of, for example, 50° C. to 150° C., preferably 60° C. to 125° C., more particularly 65° C. to 100° C. Through reaction temperatures of below 100° C., in particular, it is possible effectively to prevent further reaction of polyester or diester derivatives with molecules of the hydroxy-functional component (B). It is of course also possible to use typical catalysts such as sulfuric acid or dibutyltin laurate, although the omission of such catalysts is advantageous in order to prevent the aforementioned further reaction. The polyester and diester derivatives may be obtained, for example, as a reaction mixture with organic solvents, or as solid resins or as oils, following distillation of organic solvents optionally employed.

In the ring-opening reaction, or the preparation of the polyester and diester derivatives, component (A) is reacted with component (B) preferably in such a way that the molar ratio of the anhydride groups of component (A) to the hydroxyl groups of component (B) is greater than 0.6, more preferably between 0.7 and 2.0. In one particularly advantageous embodiment of the present invention, operation is carried out such that the anhydride groups of the component (A) are present in a molar deficit with respect to the hydroxyl groups of component (B). Preferred in this case is a molar ratio of the anhydride groups of component (A) to the hydroxyl groups of component (B) of 0.7 to less than 1.0, more particularly 0.8 to 0.95. In this way there is complete conversion of the anhydride, and so virtually no anhydride molecules remain in the reaction mixture after the reaction. The stated molar ratios are to be understood as ratios calculated from the respective functionality of the starting compounds used. In the case of component (B1), therefore, in addition to the mass employed, the OH number measured is employed as a basis for calculation. In the case of the monomeric starting compounds (component (B2), anhydride (A)), the molar amount of functional groups is a product of the molecular weight and of the mass employed.

The polyester derivatives preferably have an OH number of 0 to 50, more preferably of 2 to 30, very preferably of 5 to 25 mg KOH/g. With particular preference, therefore, the derivatives contain only a very small fraction of hydroxyl groups, attributable, for example, to a nonquantitative conversion that is a result purely of synthesis. The acid number of the polyester derivatives is preferably higher, as a result of the carboxyl groups resulting from the anhydride, and more preferably is in the range from 50 to 200 mg KOH/g, preferably 70 to 140 mg KOH/g.

The number-average molecular weight of the polyester derivatives is preferably in the range from 600 to 3000 g/mol, more preferably 900 to 2000 g/mol, while the weight-average molecular weight is preferably in the range from 1600 to 3600 g/mol, more preferably 2000 to 3000 g/mol.

It follows from what has been said above that the diester derivatives are preferably dicarboxy-functional, i.e., have two carboxyl groups. Hence there are preferably only a few hydroxyl groups in the diester derivatives that remain as a result, for example, of an incomplete reaction of component (B2). The OH number is preferably from 0 to 50, more preferably from 2 to 30, very preferably from 5 to 25 mg KOH/g. This small fraction of hydroxyl groups is of course synonymous with an on average somewhat lower number of carboxyl groups per molecule, in other words, in particular, a number on average slightly lower than 2 carboxyl groups per molecule. For the diester derivatives as well, the acid number may be determined as described above, and is preferably from 100 to 250 mg KOH/g, more preferably 125 to 225 mg KOH/g, very preferably from 150 to 200 mg KOH/g.

Aqueous Composition

The aqueous composition of the invention comprises at least one polyester and/or diester derivative of the invention, and water. The aqueous compositions preferably consist to an extent of at least 80 wt %, preferably at least 90 wt %, of at least one polyester and/or diester derivative of the invention, and water. Additionally present there may be, for example, neutralizing agents, more particularly the neutralizing agents described later on below.

Aqueous in the context of the present invention means that organic solvents are entrained, for example, merely as residual fractions or impurities, through residual fractions, for example, of organic solvents which were used in the preparation of the polyester and diester derivatives and which could possibly not be removed completely by distillation. Aqueous means more particularly that the fraction of organic solvents is less than 5 wt %, preferably less than 2 wt %, based in each case on the total weight of the aqueous composition. With very particular preference the aqueous composition is free from organic solvents. The expression "aqueous" is preferably, in particular, to be understood to mean that the preparation comprises at least 30 wt % of water, preferably at least 35 wt % of water, more particularly 35 to 80 wt % of water, and very preferably 45 to 75 wt % of water.

In spite of the hydrophobic groups which come from component (B), the polyester and diester derivatives can be introduced into water, on the basis of their carboxyl groups which come from component (A) and on the basis of the consequent suitability for forming anions. Such a process can, as is known, be made more effective by deliberate neutralization of groups capable of forming anions, especially carboxyl groups. The carboxylic acid groups of the polyester and diester derivatives, accordingly, are preferably neutralized before or during the addition of water, preferably before the addition of water, with corresponding neutralizing agents. For the neutralization of the carboxyl groups, preference is given to employing ammonia, amines and/or amino alcohols. Employed with preference are di- and triethylamine, dimethyl-aminoethanol, diisopropanolamine, morpholines and/or N-alkylmorpholines.

The molar ratio of groups capable of neutralization, from the neutralizing agent, more particularly primary, secondary, and tertiary amino groups, to carboxylic acid groups is preferably greater than 0.7, more preferably between 0.75 and 1.5, more particularly between 0.8 and 1.3, and very preferably between 0.85 and 1.2. In this way a significant fraction of the carboxylic acid groups can be neutralized or else a degree of neutralization of approximately 1 can be achieved.

The fraction of the polyester and/or diester derivatives in the aqueous compositions, based on the total amount of the composition, is situated for example in the range from 20 to 65 wt %, preferably 25 to 55 wt %. The fraction of the polyester or diester derivatives is determined via the solids (for method of determination, see above).

The polyester and diester derivatives of the invention form liquid-crystalline phases with water.

The liquid-crystalline phases in the aqueous compositions may form spontaneously, in other words by addition of the polyester and/or diester derivative to water, liquid-crystalline phases are formed, and so aqueous compositions comprising liquid-crystalline phases are produced. It is also possible for the liquid-crystalline phases to be formed by deliberate dilution of the polyester and diester derivatives in water, in other words by specific establishment of a defined fraction of the polyester or diester derivative in water, more particularly in the fractional ranges indicated above.

A preferred process for preparing liquid-crystalline phases is described below.

The polyester or diester derivatives, present, following their preparation, for example, in the form of solid resin or else in a mixture with organic solvents, are admixed with neutralizing agents. Then the organic solvent, where present, is removed by distillation, and water is added. The water added may be at room temperature, in other words may have a temperature of between 18 and 25° C., or else may be slightly heated, to 50 to 70° C., for example. The temperature of the water is set preferably at 18 to 70° C. This water is preferably added dropwise, so that the polyester or diester derivatives are gradually diluted with water. Adjustment is then made to the desired concentration of polyester or diester derivative; more particularly, the abovementioned preferred amounts or fractions are established.

An alternative option, after the addition of the neutralizing agent, is for only an initial amount of water to be added first, and then the organic solvent, where present, to be removed by distillation. The initial amount of water is preferably selected so that following the addition of the water and the distillative removal of any organic solvent present, the resulting fraction of the polyester or diester derivative is from 70 to 85 wt %. This water preferably likewise has a temperature of 18 to 70° C. Thereafter, again the gradual dilution to the desired fraction (solids or non-volatile fraction) of the polyester or diester derivative takes place.

With a polyester or diester derivative content of 20 to 65 wt % in particular, preferably 25 to 55 wt %, the aqueous compositions have particularly pronounced liquid-crystalline properties—in other words, the aqueous compositions in that case comprise pronounced liquid-crystalline phases.

In another particular embodiment of the present invention, the aqueous compositions further comprise layered hydroxides, more particularly layered double hydroxides. The amount of these layered hydroxides is for example from 2 to 20 wt %, very preferably 3 to 10 wt %.

Layered hydroxides, more particularly double hydroxides (layered double hydroxides, LDH) and their preparation are known to the skilled person and are described for example in WO 2013056846 A1.

The LDH to be used advantageously in the context of the present invention are described by the formula (II):

$$[M^{2+}_{(1-x)}M^{3+}_{x}(OH)_2][A^{y-}_{(x/y)}]\cdot nH_2O \qquad (II)$$

where $M^{2+}$ stands for divalent metallic cations, and the $M^{2+}$ are preferably selected from the group consisting of $Zn^{2+}$, $Mg^{2+}$, $Ca^{2+}$, $Cu^{2+}$, $Ni^{2+}$, $Co^{2+}$, $Fe^{2+}$, $Mn^{2+}$, $Cd^{2+}$, $Pb^{2+}$, $Sr^{2+}$, and mixtures thereof, preferably $Zn^{2+}$, $Mg^{2+}$, $Ca^{2+}$, and mixtures thereof, very preferably $Zn^{2+}$ and/or $Mg^{2+}$, more particularly $Zn^{2+}$, $M^{3+}$ stands for trivalent metallic cations, and the $M^{3+}$ are preferably selected from the group consisting of $Al^{3+}$, $Bi^{3+}$, $Fe^{3+}$, $Cr^{3+}$, $Ga^{3+}$, $Ni^{3+}$, $Co^{3+}$, $Mn^{2+}$, $V^{3+}$, $Ce^{3+}$, $La^{3+}$, and mixtures thereof, preferably $Al^{3+}$, $Bi^{3+}$ and/or $Fe^{3+}$, more particularly $Al^{3+}$, $A^{y-}$ stands for organic and inorganic anions, and the $A^{y-}$ are preferably selected from the group consisting of carbonate, chloride, nitrate, hydroxide, bromide, molybdate, chromate, salicylate, oxalate, 2,4-dimercapto-1,3,4-thiadiazole and its derivatives, EDTA, benzotriazolate, organic anions of amino acids, more particularly alpha-amino acids, preferably alanine, arginine, asparagine, aspartic acid, cysteine, cystine, glutamine, glutamic acid, histidine, isoleucine, leucine, lysine, methionine, phenylalanine, proline, serine, threonine, tryptophan, tyrosine, valine, selenocysteine, pyrrolysine, and selenomethionine, and also organic anions of the following formula (III):

(III)

where $R_1$=COO$^-$ or SO$_3^-$ and $R_2/R_3$=NH$_2$, OH, or H, and preferably $R_2$=$R_3$=H is excluded;

x has a value of 0.05 to 0.5, more particularly 0.15 to 0.4, very preferably of 0.25 to 0.35, and n has a value of 0 to 10.

Particularly preferred anions are organic anions, more particularly organic anions of alpha-amino acids, and those of the formula (III).

On account of their liquid-crystallinity and the attendant balance between anisotropy and fluidity, and also on account of the further performance properties that can be correlated with these features, examples being effects on pigment orientation and rheology of aqueous systems, in conjunction with good formulating qualities, the liquid-crystalline phases form a highly promising basis for a variety of applications.

Examples of potential uses include aqueous automotive and industrial coatings, which often are intended to have a brightness and/or color effect that is highly dependent on the viewing angle, and in which the liquid paint materials are to have a high nonvolatile fraction, but at the same time are to be sprayed with high discharge rates. In this context in particular, the effect on pigment orientation and simultaneously good formulating properties as a result of the liquid-crystallinity are particularly profitable. Other applications include organic anticorrosion coatings for metallic substrates, which are intended to combine a high diffusion barrier for oxygen and moisture with effective dissipation of energy in the event of penetrating projectiles (stone chipping in the case of vehicles, for example). Since some of the anisotropic liquids may consist of extended, porous lamellae, with a defined pore size in the range of a few nanometers, they can also be conceived as readily accessible starting formulations for separation membranes.

The invention is illustrated below using examples.

EXAMPLES

Unless otherwise noted, all of the measurement data reported in the examples were obtained in accordance with the methods of determination that have been specified in the general part of the description.

1. Preparation of Inventive Polyester and Diester Derivatives 1.1 Preparation of a Polyester (B1)

A polyester (B1) is prepared as follows: a reactor with anchor stirrer, nitrogen inlet and water separator with overhead temperature measuring means and top-mounted pack column with reflux condenser is charged with 44.40 g of fully hydrogenated bisphenol A, 7.07 g of cyclohexane-1,2-dicarboxylic anhydride, 23.41 g of dimeric fatty acid (Pripol®1012, from Unichema, based on unsaturated C18 fatty acid derivatives and having a dimer content of at least 97 wt %, a trimer content of not more than 1 wt %, and not more than traces of monomer content). Under a nitrogen atmosphere and with stirring, the contents of the reactor are heated at 190 degrees C. until the reaction mixture reaches an acid number of 8-12 mg KOH/g. The overhead temperature ought not to exceed 100° C. After 9 days an acid number of 11.4 mg KOH/g is reached and the reaction mixture is cooled. 1.7 ml of water are collected from the condensation reaction. The yield is 72.7 g of solid resin. The resin possesses an OH number of 143 mg KOH/g, a mass-average molecular weight of 1884 g/mol, and a number-average molecular weight of 753 g/mol.

1.2 Preparation of an Inventive Polyester Derivative EP1

An inventive polyester derivative EP1 is prepared as follows: the resin melt of the polyester (B1) obtained in example 1.1 is admixed with 27 g of 2-butanone and dissolved with stirring in a reactor with anchor stirrer, nitrogen inlet and reflux condenser, and 35.7 g of 2-octenylsuccinic anhydride (0.9 equivalent in relation to the molar amount of hydroxyl groups in the polyester (B1) employed) are added. In a nitrogen atmosphere, the mixture is heated to 95 degrees C. and stirred at this temperature under reflux for 18 hours. The clear, colorless solution obtained in this way possesses a nonvolatile fraction of 68.4 wt % (fraction of the polyester derivative EP1). The acid number is 97 mg KOH/g. The resin possesses an OH number of 18 mg KOH/g, a weight-average molecular weight of 2218 g/mol and a number-average molecular weight of 1181 g/mol.

1.3 Preparation of an Inventive Diester Derivative ED1

An inventive diester derivative ED1 is prepared as follows: 12.6 g of fully hydrogenated bisphenol A (component (B2)) are dissolved in 23 g of 2-butanone in a reactor with anchor stirrer, nitrogen inlet and reflux condenser, and 20.4 g of n-octenylsuccinic anhydride (0.9 equivalent in relation to the molar amount of hydroxyl groups in the hydrogenated bisphenol A) are added. In a nitrogen atmosphere, the mixture is heated to 95 degrees C. and stirred at this temperature under reflux for 22 hours. The clear, colorless solution obtained in this way possesses a nonvolatile fraction of 70.1 wt % (fraction of the diester derivative ED1). The acid number is 175 mg KOH/g. The resin possesses an OH number of 27 mg KOH/g, a weight-average molecular weight of 841 g/mol and a number-average molecular weight of 701 g/mol.

2. Preparation of a Noninventive Polyester Derivative VP1

The polyester derivative VP1 is prepared as follows: the resin melt of the polyester (B1) obtained in example 1.1 is admixed with 8.35 g of 1,2,4-benzenetricarboxylic anhydride. The reactor is operated with water separator and reflux condenser, without a packed column. The mixture is heated to 160° C. and is stirred at that temperature for 25 hours. The yield is 79.02 g of solid resin. The acid number is 32.5 mg KOH/g. It is possible to collect 0.6 ml of water as a result of the condensation reaction. The resin possesses an OH number of 68 mg KOH/g, a weight-average molecular weight of 7188 g/mol, and a number-average molecular weight of 2171 g/mol.

3. Production of Aqueous Compositions and Liquid-Crystalline Phases 3.1 Production of Inventive Aqueous Compositions Comprising EP1

In a reactor with anchor stirrer, nitrogen inlet, reflux condenser, and distillation bridge, the solution (containing EP1) obtained in example 1.2 is heated to 80 degrees C., under nitrogen and with stirring, and is admixed with 10.19 g of N,N-dimethylamino-2-ethanol, corresponding to a degree of neutralization of 0.95 of the carboxyl groups of the polyester derivative as determined via the acid number. After further ten-minute stirring, the 2-butanone is removed by vacuum distillation at 80 degrees C. until the 2-butanone content of the remaining polyester derivative reaches <0.5 wt % (determined via gas-chromatographic analysis).

Deionized water conditioned to room temperature is added dropwise to this resin melt. The polyester derivative EP1 is diluted down from the (approximately) 100 wt % to a nonvolatile fraction of 42 wt %, initially with a mass flow rate of 2 g per minute. This is followed by stirring for 20 minutes, and a sample of the corresponding aqueous composition is taken off for the investigation described in section 4 (aqueous composition E1). The remaining dispersion is subsequently diluted down in turn, by dropwise addition of deionized water conditioned at room temperature, to a nonvolatile fraction of 33 wt %, with a mass flow rate of 2 g per minute (aqueous composition E2). The aqueous compositions are cooled to room temperature and set aside for 3 days for the further characterization (section 4).

3.2 Production of Inventive Aqueous Compositions Comprising ED1

In a reactor with anchor stirrer, nitrogen inlet, reflux condenser, and distillation bridge, the solution (containing EP1) obtained in example 1.3 is heated to 80 degrees C., under nitrogen and with stirring, and is admixed dropwise with 12.4 g of N,N-dimethylamino-2-ethanol, corresponding to a degree of neutralization of 0.95 of the carboxyl groups of the diester derivative as determined via the acid number. Then 24.3 g of water are added with stirring. The 2-butanone is removed by vacuum distillation at 80 degrees C. until the 2-butanone content of the remaining diester derivative reaches <0.5 wt % (determined via gas-chromatographic analysis).

This dispersion possesses a nonvolatile fraction of 76 wt % and is diluted down with water to a nonvolatile fraction of 40 wt %, by dropwise addition, with a mass flow rate of 2 g per minute, at 60 degrees C. (aqueous composition E3). The aqueous compositions are cooled to room temperature and set aside for 3 days for further characterization (section 4).

3.3 Production of Noninventive Aqueous Compositions Containing VP1

In a reactor with anchor stirrer, nitrogen inlet, reflux condenser, and distillation bridge, the resin obtained in example 2 is admixed with 33.5 g of 4-methylpentan-2-one and left to stand over a period of 5 days for complete dissolution. The resulting mixture is heated to 90 degrees C. under a nitrogen atmosphere and with stirring, and is admixed over the course of 10 minutes with 3.9 g of N,N-dimethylamino-2-ethanol, corresponding to a degree of neutralization of 0.95 of the carboxyl groups of the polyester derivative, as determined by the acid number. After cooling to 80 degrees C., 47.8 g of water are added over the course of 120 minutes with stirring. The 4-methylpentan-2-one is removed by vacuum distillation at 73 degrees C., until the amount of 4-methylpentan-2-one in the remaining polyester derivative reaches <0.5 wt % (determined via gas-chromatographic analysis).

This dispersion possesses a nonvolatile fraction of 61 wt % and is diluted down with water to a nonvolatile fraction of 36 wt %, by dropwise addition, with a mass flow rate of 2 g per minute at 73 degrees C. The temperature of 73 degrees C. is held for 4 hours and the dispersion is homogenized with continual stirring (aqueous composition V1). The aqueous compositions are cooled to room temperature and set aside for 3 days for the further characterization (section 4).

Table 1 gives an overview, again, of the aqueous compositions prepared

TABLE 1

| Aqueous composition | Derivative contained | Fraction of derivative (nonvolatile fraction) in wt % |
| --- | --- | --- |
| E1 | EP1 | 42 |
| E2 | EP1 | 33 |
| E3 | ED1 | 40 |
| V1 | VP1 | 36 |

4. Performance Investigation of the Aqueous Compositions

The aqueous compositions obtained in section 3 were investigated as follows.

4.1 Optical Microscopy Under Light with Crossed Polarization (OM)

Using OM it is possible to detect the conventional phenomenon of birefringence. Whereas with birefringent phases, such as crystalline phases, for example, in the case of the crossed polarizer arrangement (primary filter or linear polarizer of the light from the light source, and also secondary filter, or analyzer, rotated by 90° relative to the primary filter) light penetrates the analyzer and hence correspondingly bright areas can be seen on the resulting microscopy images, this is not the case with purely isotropic phases. In the case of the latter, therefore, there is complete extinction; the images are dark or completely black. If, therefore, light regions are visible, a crystalline (anisotropic, ordered) character can be concluded.

The OM was recorded on an Olympus BX 51 microscope with XC 10 digital camera and UM Plan FI lenses. A sample of the respective aqueous composition (E1 to E3, V1) was prepared between a slide and a cover glass. The sample is brought to a volume of approximately 100 μm, by the pressing together of slide and cover glass, and is left to stand for at least a minute, in order to allow the slightly sheared sample to relax in this way. Measurement takes place at room temperature in transmitted light, with polarization filters crossed at 90 degrees.

Under the microscope, samples E1 to E3 (inventive aqueous compositions) show distinctly pronounced regions in which light penetrates through the analyzer. The birefringence of the inventive phases shows that there are anisotropic ordered structures present, whose "oily streak" textures fit with lamellar liquid-crystalline phases. The comparative sample V1 likewise exhibits birefringence.

The aforementioned properties can also be seen from FIGS. 1 to 4.

All four aqueous compositions therefore exhibit ordered, anisotropic phases.

4.2 Rheology Characterization of the Aqueous Compositions

Using the aqueous compositions E1 to E3 and V1, amplitude sweeps at 23° C. were conducted on an Anton Paar MCR501 with a CP50/1 measuring geometry over a shear stress range from 0.2 Pa (or 0.5/2 Pa) to 100 Pa, during which the storage modulus G' and the loss modulus G" of the respective aqueous composition were measured.

While the storage modulus G' is an expression of elasticity of a sample (that is, in other words, the elastic, e.g. gellike properties of a sample, and hence reflects the elastic deformation which takes place after introduction of energy), the loss modulus G" reflects the dissipatively released or lost viscous component of the energy introduced into the sample, and is therefore an expression, in principle, of a fluid character.

Systems where the storage modulus G' is significantly larger than the loss modulus G" have virtually no fluid character at all, and therefore, in particular, are not flowable. In contrast to the fluid and flowable character, such systems generally have a gellike character, leading particularly to distinctly hindered formulating properties and deployability. For example, gellike systems of this kind are able only with difficulty to form homogeneous mixtures with other components.

Systems where the loss modulus G' is greater than the storage modulus G' are generally flowable systems which are therefore easy to formulate. The same applies to systems in which the loss modulus G" and the storage modulus G' are in a similar order of magnitude. Systems of this kind, known as viscoelastic fluids, likewise have the fluid character necessary for good formulating qualities.

The inventive compositions have loss modulus G" and storage modulus G' in approximately the same order of magnitude over a wide shear stress range (0.2 to 100 Pa).

Figure 1:
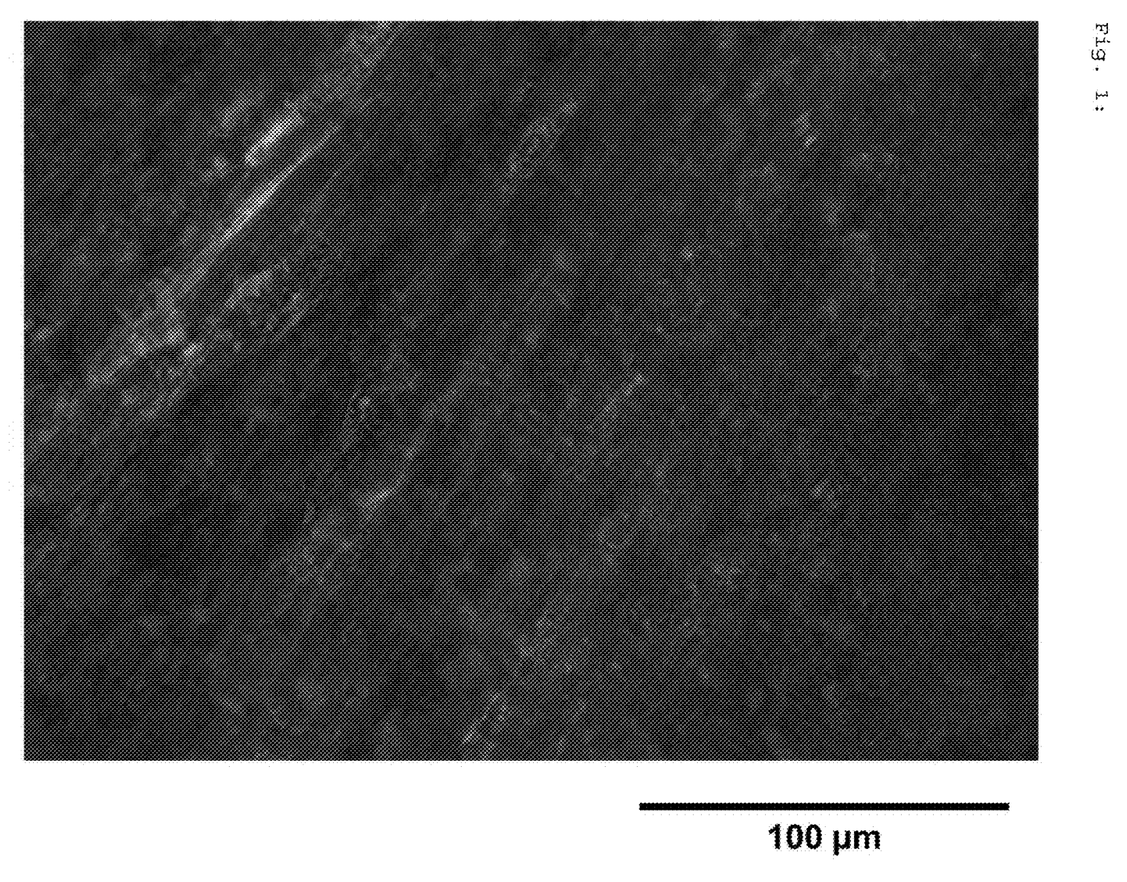
FIG. 1:
Microscope image (optical microscopy under cross-polarized light) of aqueous preparation E1.
Figure 2:
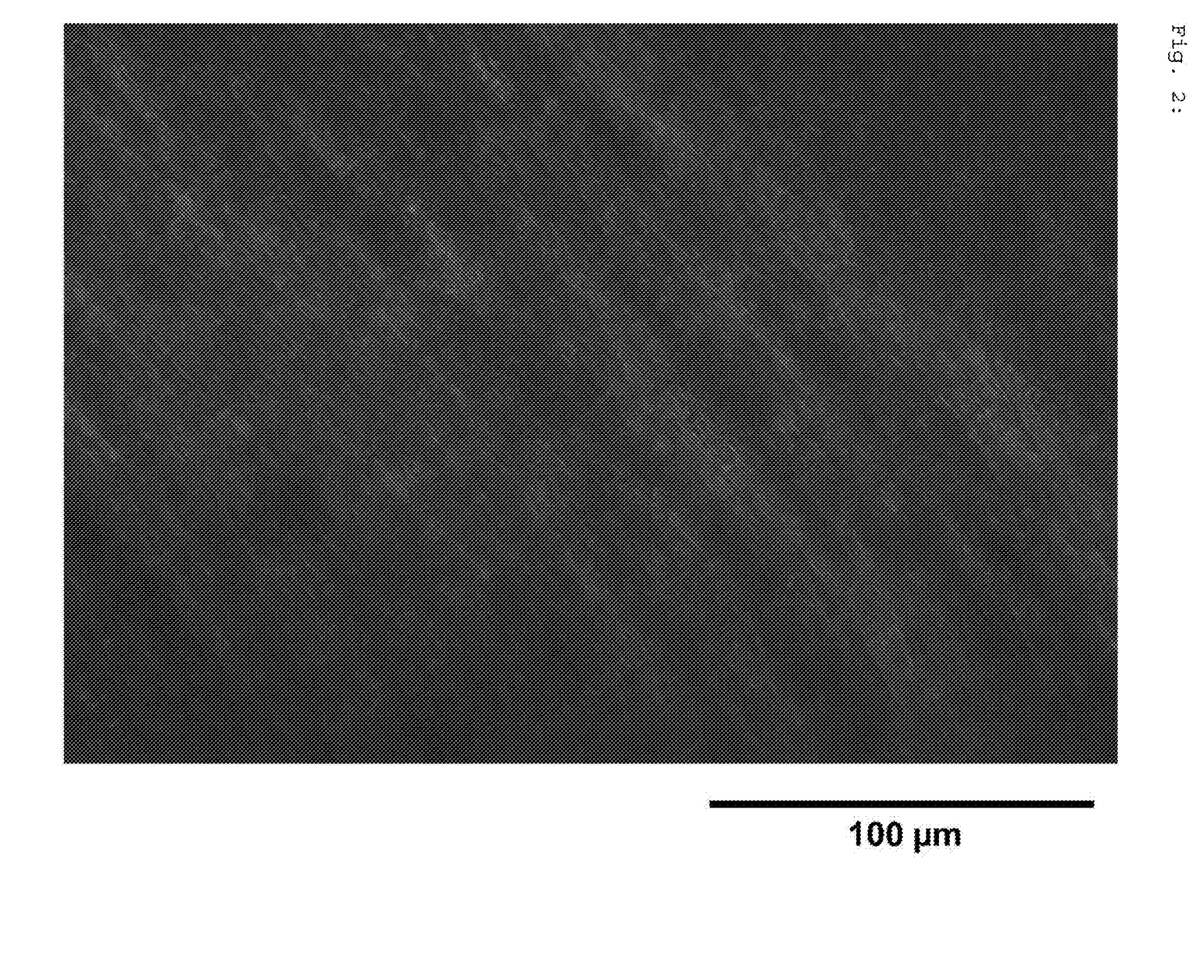
FIG. 2:
Microscope image (optical microscopy under cross-polarized light) of aqueous preparation E2.
Figure 3:
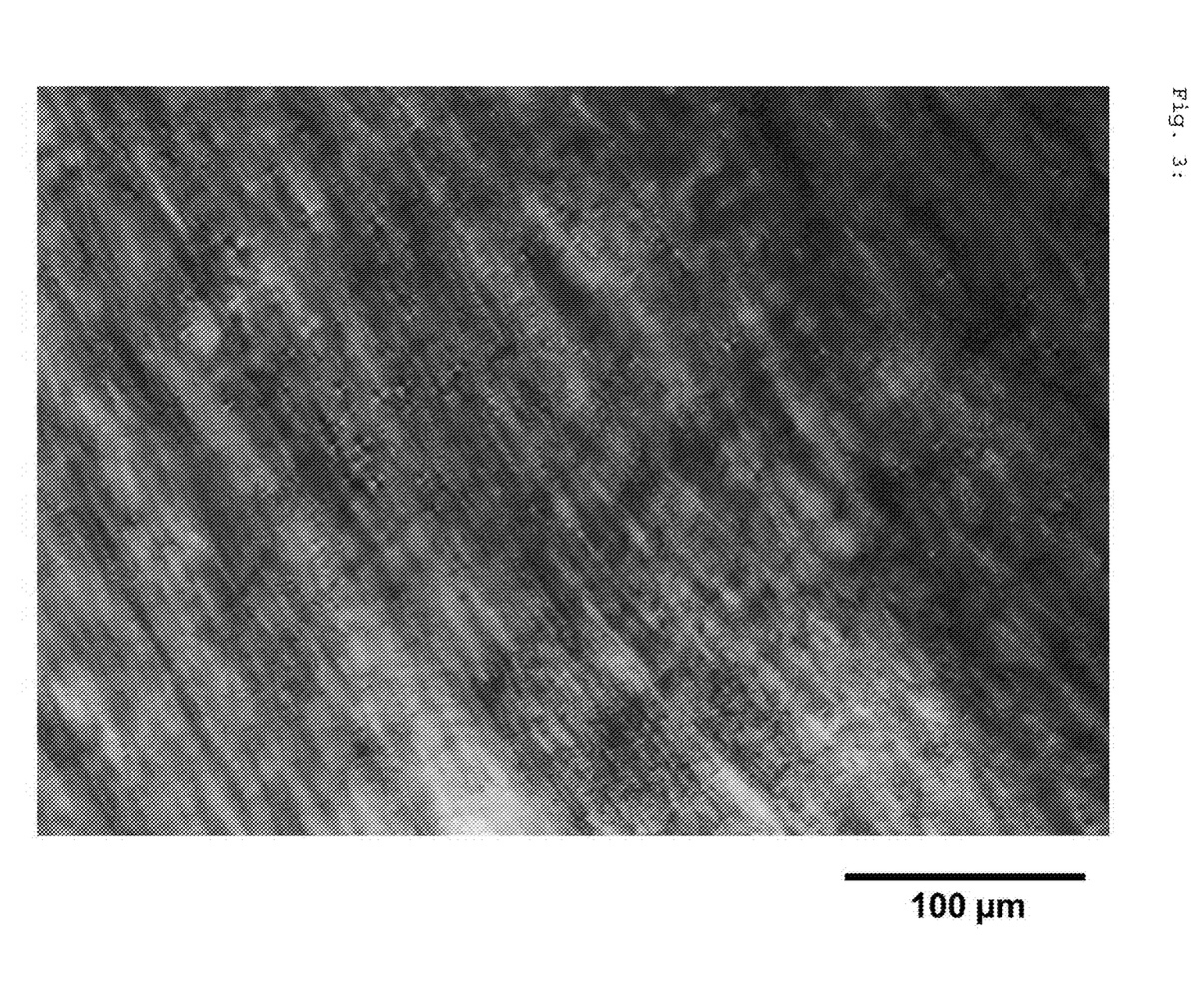
FIG. 3:
Microscope image (optical microscopy under cross-polarized light) of aqueous preparation E3.
Figure 4:
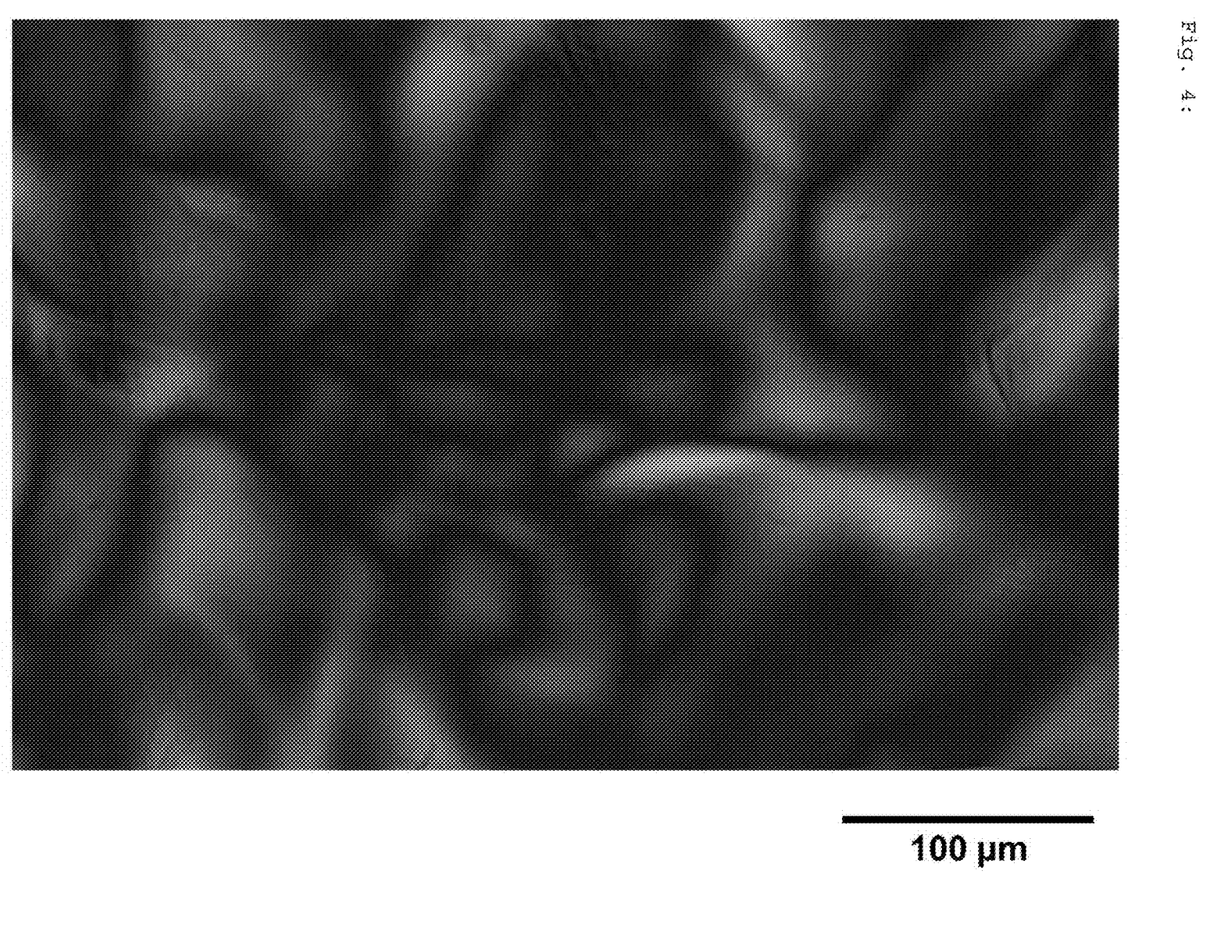
FIG. 4:
Microscope image (optical microscopy under cross-polarized light) of aqueous preparation V1.
Figure 5:
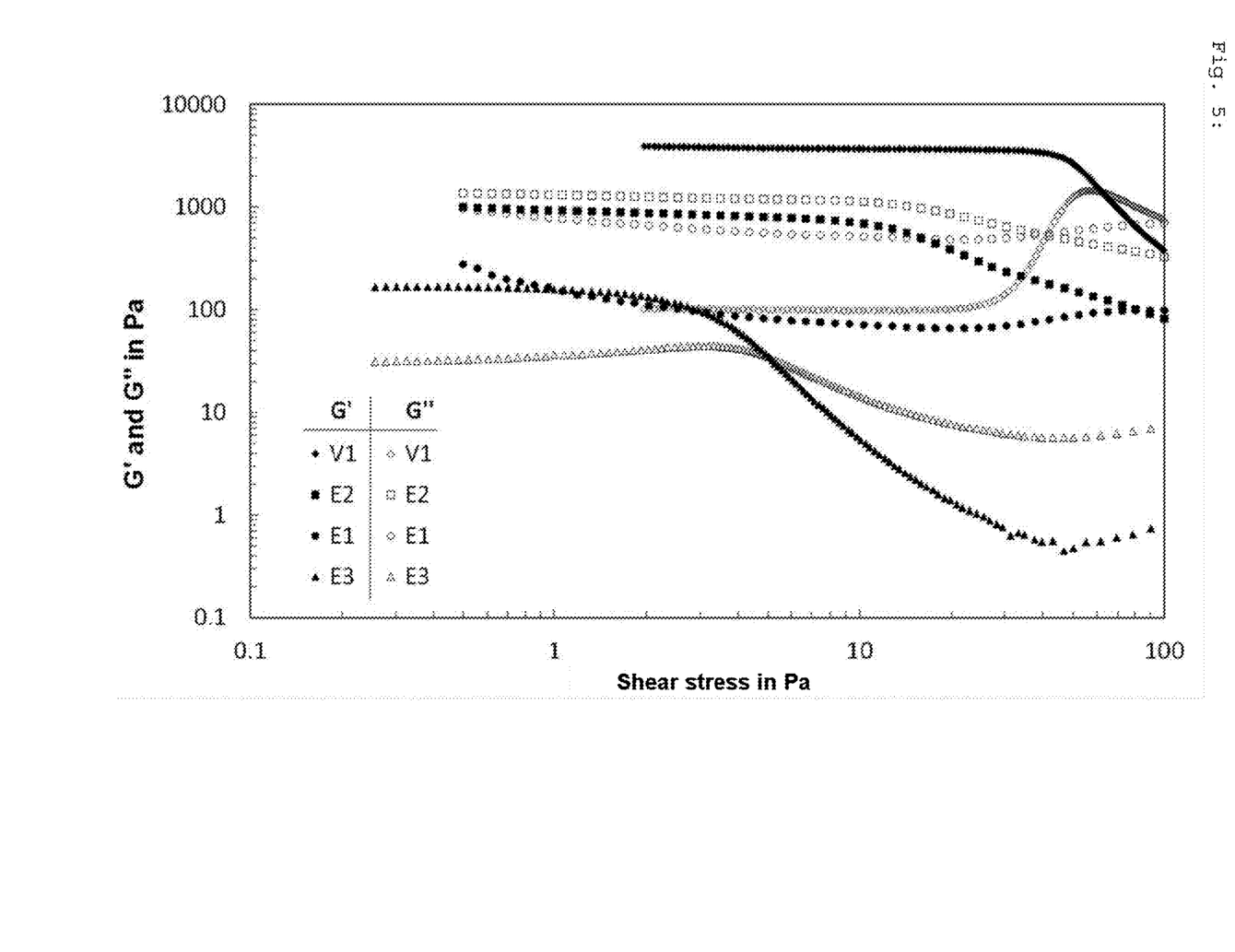
FIG. 5:
Storage modulus (G') and loss modulus (G") of aqueous compositions E1, E2, E3, and V1, plotted against the shear stress.

Thus, for example, the amounts of loss modulus G" and storage modulus G' at a shear stress of 10 Pa differ by only about 442 Pa (composition E1), 434 Pa (composition E2), and 34 Pa (composition E3), with the loss modulus G" being greater than the storage modulus G' in each case. Similar conditions also come about at higher or lower shear stresses. The moduli are each in a similar order of magnitude, with the loss modulus G" being greater over the entire range for the compositions E1 and E2 than the storage modulus G', and with the storage modulus being only slightly larger than the loss modulus for the composition E3 at shear stresses of below 5 Pa (FIG. 5 shows the loss modulus and the storage modulus for the samples measured, over the entire measured range of the shear stress).

These data fit very well with the macroscopic states of the compositions that can be detected purely visually. All three samples are fluid and hence have good formulating qualities. They therefore combine a crystalline, anisotropic, and ordered state with a pronounced fluidity, and with the good formulating properties which follow therefrom. They are therefore liquid-crystalline.

In contrast, in the case of the noninventive sample V1, a much greater storage modulus G' than loss modulus G" is observed over a wide shear stress range. At a shear stress of 10 Pa, the storage modulus is greater by about 3700 Pa than the loss modulus. The difference here, then, is significantly greater than in the case of the inventive systems.

The data fit very well, in turn, with the macroscopic state of the composition, as detectable by purely visual means. Composition V1 is a nonfluid gel which cannot be processed with customary laboratory stirrers or else with larger stirring devices such as dissolvers, and, correspondingly, has very poor formulating properties.

It is therefore found that the compositions of the invention preserve their liquid-crystalline character over a wide range of mechanical stress (shear stress), whereas the noninventive composition has a gellike character.

The invention claimed is:

1. A carboxy-functional polyester or diester derivative obtained by ring-opening reaction of
   (A) at least one anhydride of formula (I)

(I)

where $R_1$=H, $C_1$ to $C_{48}$ alkyl, or $C_2$ to $C_{48}$ alkenyl, with
   (B) at least one hydroxy-functional component, where
   (B1) the polyester derivative is prepared using at least one linear polyester having two terminal hydroxyl groups prepared using 7 to 95 mol %, based on the total amount of the monomers used in preparing the polyester (B1), of at least one difunctional monomer (b1) with aliphatic groups with 12 to 70 carbon atoms between the functional groups,
   and
   (B2) the diester derivative is prepared using at least one dihydroxy-functional component which has an aliphatic group with 12 to 70 carbon atoms between the hydroxyl groups.

2. The carboxy-functional polyester or diester derivative of claim 1, wherein for the formula (I) $R_1$ is H and/or $C_6$ to $C_{48}$ alkenyl.

3. The carboxy-functional polyester or diester derivative of claim 1, wherein the aliphatic groups of the monomer (b1) and of component (B2) have 13 to 50 carbon atoms.

4. The carboxy-functional polyester or diester derivative of claim 1, wherein the monomer (b1) is selected from the group consisting of a fully hydrogenated bisphenol, a dimeric aliphatic fatty alcohol, and a dimeric aliphatic fatty acid.

5. The carboxy-functional polyester or diester derivative of claim 1, wherein the polyester (B1) has a hydroxyl number of 80 to 200 mg KOH/g.

6. The carboxy-functional polyester or diester derivative of claim 1, wherein component (B2) is at least one member selected from the group consisting of a fully hydrogenated bisphenol and a dimeric aliphatic fatty alcohol.

7. The carboxy-functional polyester or diester derivative of claim 1, wherein a molar ratio of anhydride groups of component (A) to hydroxyl groups of component (B) in the ring-opening reaction is from 0.7 to less than 1.0.

8. The carboxy-functional polyester or diester derivative of claim 1, having an acid number of between 50 and 250 mg KOH/g.

9. The carboxy-functional polyester or diester derivative of claim 1, having an OH number of 2 to 30 mg KOH/g.

10. The carboxy-functional polyester or diester derivative of claim 1, wherein the polyester (B1) is prepared using 60 to 90 mol %, based on the total amount of the monomers used in preparing the polyester (B1), of at least one monomer (B1).

11. A process for preparing the polyester or diester derivative of claim 1, comprising reacting
    (A) at least one anhydride of formula (I)

(I)

where $R_1$=H, $C_1$ to $C_{48}$ alkyl, or $C_2$ to $C_{48}$ alkenyl, with
    (B) at least one hydroxy-functional component, with opening of the anhydride ring, where (B1) the polyester derivative is prepared using at least one linear polyester having two terminal hydroxyl groups prepared using 7 to 95 mol %, based on the total amount of the monomers used in preparing the polyester (B1), of at least one difunctional monomer (b1) with aliphatic groups with 12 to 70 carbon atoms between the functional groups,
and
(B2) the diester derivative is prepared using at least one dihydroxy-functional component which has an aliphatic group with 12 to 70 carbon atoms between the hydroxyl groups.

12. An aqueous composition comprising the polyester derivative or diester derivative of claim 1, and water.

13. The aqueous composition of claim 12, further comprising a neutralizing agent selected from the group consisting of ammonia, an amine, and an amino alcohol.

14. The aqueous composition of claim 12, wherein the amount of the polyester derivative and/or diester derivative, based on the overall constitution, is 20 to 65 wt %.

15. A liquid-crystalline phase comprising the polyester or diester derivative of claim 1.

16. A carboxy-functional polyester or diester derivative obtained by ring-opening reaction of (A) at least one anhydride of formula (I)

(I)

where $R_1$=a $C_1$ to $C_{48}$ alkyl or a $C_2$ to $C_{48}$ alkenyl,
with
(B) at least one hydroxy-functional component, where
(B1) the polyester derivative is prepared using at least one linear hydroxy-functional polyester prepared using 7 to 95 mol %, based on the total amount of the monomers used in preparing the polyester (B1), of at least one difunctional monomer (b1) with aliphatic groups with 12 to 70 carbon atoms between the functional groups,
and
(B2) the diester derivative is prepared using at least one dihydroxy-functional component which has an aliphatic group with 12 to 70 carbon atoms between the hydroxyl groups.

\* \* \* \* \*